United States Patent
Xueping et al.

(10) Patent No.: US 8,834,637 B2
(45) Date of Patent: Sep. 16, 2014

(54) BIOCHEMICAL ANALYZER AND METHOD FOR CLEANING FLUID COMPONENTS OF THE SAME

(75) Inventors: Jiang Xueping, Shenzhen (CN); Zhang Tao, Shenzhen (CN); Shi Xueyuan, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1231 days.

(21) Appl. No.: 12/608,834

(22) Filed: Oct. 29, 2009

(65) Prior Publication Data

US 2010/0108097 A1    May 6, 2010

(30) Foreign Application Priority Data

Oct. 30, 2008   (CN) .......................... 2008 1 0217188

(51) Int. Cl.
*B08B 7/02* (2006.01)
*B08B 5/04* (2006.01)
*B08B 9/027* (2006.01)
*B08B 9/00* (2006.01)
*B08B 5/00* (2006.01)
*B01L 99/00* (2010.01)
*G01N 35/10* (2006.01)
*B01L 3/00* (2006.01)
*G01N 35/04* (2006.01)

(52) U.S. Cl.
CPC . *B08B 9/00* (2013.01); *B01L 99/00* (2013.01); *B01L 3/5082* (2013.01); *G01N 35/1002* (2013.01); *G01N 2035/0437* (2013.01)
USPC ......... 134/18; 134/21; 134/22.11; 134/22.12; 134/32

(58) Field of Classification Search
CPC .......... B08B 9/00; B08B 9/032; B08B 9/027; B08B 9/04
See application file for complete search history.

(56) References Cited

U.S. PATENT DOCUMENTS

| | | | | |
|---|---|---|---|---|
| 4,641,674 A | * | 2/1987 | Batjer et al. | 134/138 |
| 5,783,450 A | * | 7/1998 | Yoshida et al. | 436/161 |
| 6,500,388 B1 | * | 12/2002 | Nagaoka et al. | 422/64 |

FOREIGN PATENT DOCUMENTS

| | | |
|---|---|---|
| CN | 2632678 Y | 8/2004 |
| CN | 200989905 Y | 12/2007 |
| FR | 2464476 A | 3/1981 |
| JP | 2004-301767 A | 10/2004 |

OTHER PUBLICATIONS

Chinese International Search Report dated Aug. 4, 2009 for China Patent Application No. 200810217188.X.
English Abstract for CN200989905, Publication date: Dec. 12, 2007.
English Abstract for CN2632678, Publication date: Aug. 11, 2004.
English Abstract for JP2004-301767, Publication date: Oct. 28, 2004.
English Abstract for FR2464476, Publication date: Mar. 6, 1981.

* cited by examiner

*Primary Examiner* — Eric Golightly
*Assistant Examiner* — Arlyn I Rivera-Cordero
(74) *Attorney, Agent, or Firm* — Kory D. Christensen; Stoel Rives LLP

(57) ABSTRACT

There is provided a biochemical analyzer and a method of cleaning fluid components of the same. The biochemical analyzer includes a reagent adding mechanism, a sample adding mechanism, at least one reaction cup, a cleaning mechanism and a waste pipeline connected to the cleaning mechanism. A control system is employed, wherein the control system has a cleaning mode for cleaning fluid components of the biochemical analyzer, having: a) a water injection step; and b) a water discharge. With the cleaning method, the fluid components such as the water drawing device and waste valve on the waste pipeline may be automatically cleaned without manual intervention.

5 Claims, 3 Drawing Sheets

BIOCHEMICAL ANALYZER AND METHOD FOR CLEANING FLUID COMPONENTS OF THE SAME

RELATED APPLICATION

The present application claims priority to Chinese Patent Application No. 200810217188.X, titled "Biochemical Analyzer and Method for Cleaning Fluid Components of the Same", which is filed on Oct. 30, 2008, and which is incorporated herein by reference in its entirety.

FIELD OF THE INVENTION

The present invention relates to a biochemical analyzer and a method for cleaning the fluid components of the same.

BACKGROUND OF THE INVENTION

In a fully-automatic biochemical analyzer, a reagent and a sample are mixed in a reaction cup to form a reaction solution, which is subjected to a spectrophotometry colorimetric test, and is discharged as effluent from the biochemical analyzer through a waste pump and a waste valve. In addition, to achieve the reuse of the reaction cup, it is required that the reaction cup is dunked and washed using a detergent and deionized water. The detergent and the water after washing the reaction cup are also discharged as effluent from the biochemical analyzer via the waste pump and waste valve.

It can be known from the foregoing process that the effluent from a biochemical analyzer may contain such complex elements as fat, protein, detergent, reagent, and the like. These elements may have the following adverse affects on its fluid components such as the waste pump and waste valve:

1) Elements such as fat, protein and the like, after being in contact with the fluid components such as the waste pump and waste valve for a long time, will be deposited onto the membranes thereof, finally causing the pump and valve to be blocked;

2) Elements such as detergents will lead to the formation of crystalline particles of detergents on membranes of the pump and valve as a result of volatilization in the pipes of the biochemical analyzer when the biochemical analyzer is emptied for transportation or left unused, thus causing the pump and valve to be blocked; and 3) Elements such as reagents, which may contain many complex organic ingredients, after being in contact with membranes of the pump and valve for a long time, will cause a corrosion of the pump and valve.

Therefore, it is generally required to perform periodic maintenance of the fluid components such as the pump, valve and the like. During the maintenance, the pump and valve are disassembled to have their membranes and sealing components cleaned, removing any possible impurities and crystals deposited thereon. However, as the fluid components such as the pump and valve used in a biochemical analyzer are precise components, the disassembly and cleaning thereof need to be performed by a skilled operator to avoid damages. Moreover, such maintenance requires significant amount of labor, and there may be a long interval between two maintenance actions, during which the reliability of the pump and valve can not be guaranteed. In addition, during the maintenance, the operator is exposed to a risk of biologic contamination as he directly touches the fluid components that are in contact with effluent from the biochemical analyzer for a long time.

SUMMARY OF THE INVENTION

To address the above-mentioned technical problems and overcome the disadvantages in the prior art, the present invention provides a biochemical analyzer which allows its fluid components to be cleaned automatically and ensures the reliability of its fluid components, and a method of controlling said fluid components.

According to the first aspect of the embodiment of the present invention, there is provided a method of cleaning fluid components of a biochemical analyzer, the biochemical analyzer having a reagent adding mechanism, a sample adding mechanism, at least one reaction cup, a cleaning mechanism, and a waste pipeline connected to the cleaning mechanism; the waste pipeline being provided with a waste pump; each of the reagent adding mechanism, the sample adding mechanism, the cleaning mechanism and the waste pump being electrically connected to a control system, the control system being configured to have a cleaning mode, the cleaning comprising: a) a water injection step in which the control system allows at least one of the reagent adding mechanism, the sample adding mechanism and the cleaning mechanism to inject water into at least one reaction cup; and b) a water discharge step in which the control system allows the reaction cup, the cleaning mechanism and the waste pipeline to be in fluid communication, and activates the waste pump to discharge water from the reaction cup through the cleaning mechanism and the waste pipeline.

According to the first aspect of the embodiment of the present invention, there is provided a biochemical analyzer comprising: a reagent adding mechanism, a sample adding mechanism, at least one reaction cup, a cleaning mechanism, and a waste pipeline connected to the cleaning mechanism, wherein the waste pipeline is provided with a waste pump, wherein each of the reagent adding mechanism, the sample adding mechanism, the cleaning mechanism and the waste pump is electrically connected to a control system, the control system being configured to have a cleaning mode, comprising: a) a water injection step in which the control system allows at least one of the reagent adding mechanism, the sample adding mechanism and the cleaning mechanism to inject water into at least one reaction cup; and b) a water discharge step in which the control system allows the at least one reaction cup, the cleaning mechanism and the waste pipeline to be in fluid communication, and activates the waste pump to discharge water from the at least one reaction cup through the cleaning mechanism and waste pipeline.

DETAILED DESCRIPTION OF THE INVENTION

Figure 1:
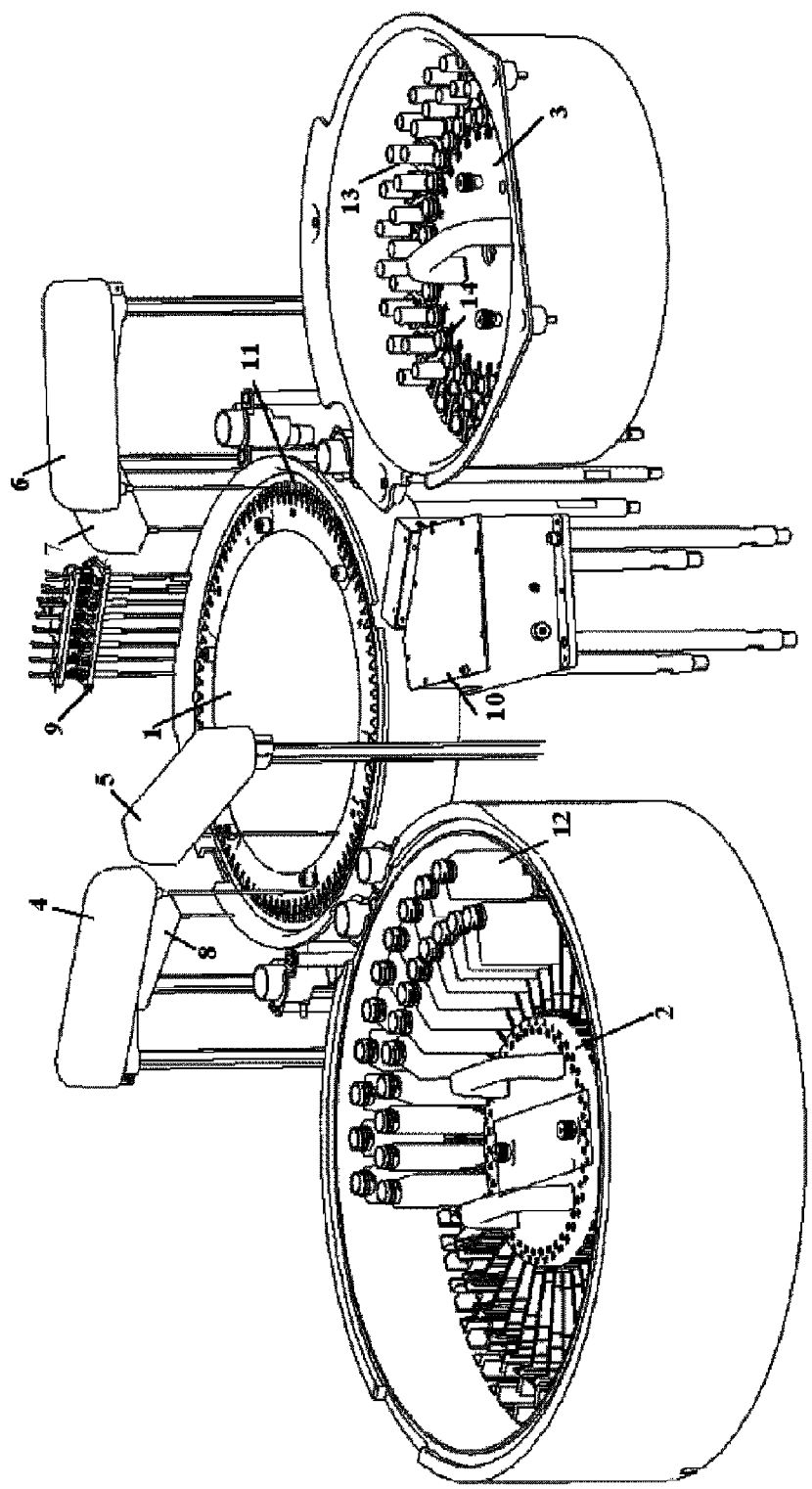
FIG. 1 is a structural schematic diagram of a biochemical analyzer.
Figure 2:
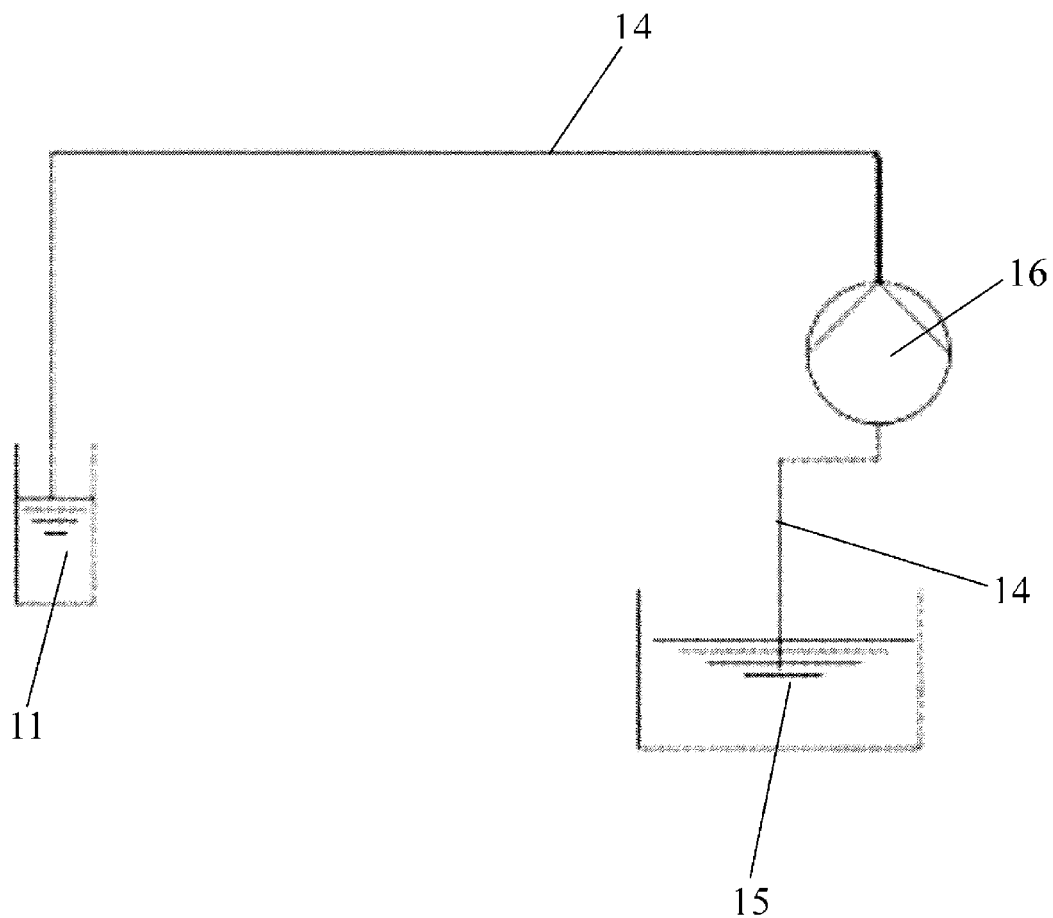
FIG. 2 is a diagram showing the structural principle in automatically cleaning the fluid components.
Figure 3:
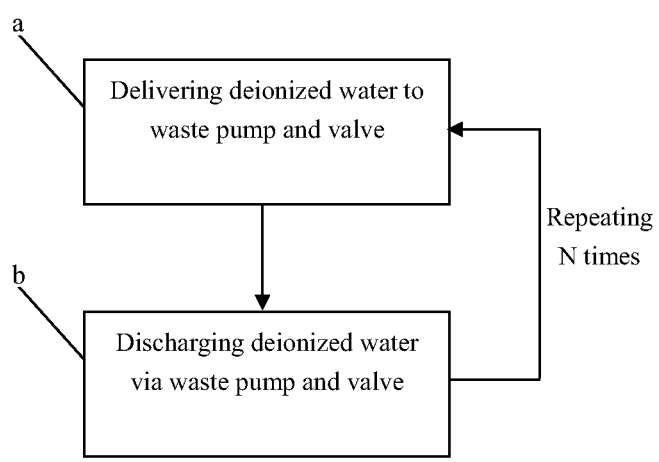
FIG. 3 is a flow chart showing a method of cleaning fluid components of a biochemical analyzer.

As shown in FIG. 1 to FIG. 3, the fluid component cleaning method according to the present embodiment is applied to a fully-automatic biochemical analyzer. The fully-automatic biochemical analyzer comprises a reaction disc 1, a reagent disc 2, a sample disc 3, a first reagent adding mechanism 4, a second reagent adding mechanism 5, a sample adding mechanism 6, a reagent stirring rod mechanism 7, a sample stirring rod mechanism 8, a cleaning mechanism 9, and an optical detection device 10.

The reaction disc 1 is arranged at a rear position in the middle of the worktable. A plurality of reaction cups 11 are disposed at an equal interval along the circumference of the reaction disc 1. A drive mechanism of the reaction disc may rotate the reaction disc 1 so as to rotate and position the plurality of reaction cups 11.

The reagent disc 2 is arranged at an anterior position on the left of the worktable. A plurality of reagent positions are equally spaced along the inner and outer circumferences of the reagent disc 2 to receive reagent bottles 12 containing first and second reagents to be used in the biochemical tests. The drive mechanism of the reagent disc may drive the reagent bottles 12 to rotate and be positioned.

The sample disc 3 is arranged at an anterior position on the right of the worktable. A plurality sample positions are equally spaced along the inner, middle and outer circumferences of the sample disc 3 to receive sample test tubes 13 containing the sample to be tested, the calibrating solution or the control solution, etc. The drive mechanism for the sample disc may cause the sample test tubes 13 to rotate and be positioned.

The first and second reagent adding mechanisms 4 and 5 are used to draw respectively first and second reagents from the reagent bottles 12, and discharge them into a corresponding reaction cup 11 on the reaction disc 1. The first and second reagent adding mechanisms 4 and 5 are arranged between the reagent disc 2 and the reaction disc 1 in tandem, wherein the first agent adding mechanism 4 is arranged at a posterior position, and the second reagent adding mechanism 5 is arranged at an anterior position, thereby avoiding space movement interference. The sample adding mechanism 6 is arranged between the sample disc 3 and the reaction disc 1 for drawing a sample to be tested from the sample test tube 13 and discharge it into a corresponding reaction cup 11 on the reaction disc 1.

The cleaning mechanism 9 is located at a rear area above the reaction disc 1, and can perform detergent washing, deionized water washing and drying of the reaction cups sequentially to ensure that the reaction cups are clean and free of residue so that they can be used again in a future biochemical test. The cleaning mechanism 9 is capable of drawing effluent from the reaction cups 11 and injecting a cleaning liquid (e.g., detergent and deionized water) into the reaction cups 11.

The sample stirring rod mechanism 8 and the reagent stirring rod mechanism 7 are both arranged along the circumference of the reaction disc 1. The reagent stirring rod mechanism 7 is responsible for stirring the first or second reagent added to the reaction cup, and the sample stirring rod mechanism 8 is responsible for stirring the sample added to the reaction cup. The optical detection device 10 is responsible for performing a spectrophotometry colorimetric test or other optical detection on the reaction cups.

The cleaning mechanism 9 is connected to the waste pipeline 14 such that effluent in the reaction cups after cleaning can be discharged into the effluent container 15 through the waste pipeline 14. At least one negative pressure waste pump 16 and at least one waste valve for connecting/disconnecting the waste pipeline 14 may be arranged on the waste pipeline 14. Effluent flows through the waste pump and valve when being discharged.

The reaction disc 1, reagent disc 2, sample disc 3, first reagent adding mechanism 4, second reagent adding mechanism 5, sample adding mechanism 6, reagent stirring rod mechanism 7, sample stirring rod mechanism 8, cleaning mechanism 9, waste pump 16 and waste valve may be coordinated and controlled by the control system, such that it is possible to perform sample adding, reagent adding, stirring, cleaning and effluent discharging in a predetermined sequence.

The control system of the biochemical analyzer is configured with a cleaning mode for cleaning the fluid components of the biochemical analyzer, the cleaning comprising: a) a water injection step for injecting water into the reaction cup 11; and b) a water discharge step for discharging, by means of the waste pump 16, water from the reaction cup 11 into the effluent container 15 through the waste pipeline 14. By repeating the above steps one or more times, the cleaning of the waste pump 16 and waste valve may be accomplished.

During cleaning, a working sequence may be set such that the control system allows the reagent adding mechanism or the sample adding mechanism to draw water either from a reagent bottle or a sample test tube filled with water beforehand or from a water source directly, and then discharge the water into a reaction cup, thereby completing the water injection step, during which the cleaning mechanism is held above the reaction cup. Then, the control system allows the cleaning mechanism to be lowered into the reaction cup to cause the reaction cup, the cleaning mechanism, the waste pipeline and the effluent container to be communicated, activates the waste pump and opens the waste valve such that water in the reaction cup is pumped out into the effluent container 15 by the waste pump 16 through the waste pipeline 14, thereby completing the water discharge step. The cleaning of the waste pump and valve can be done by repeating the above steps one or more times.

Alternatively, the working sequence can be set such that the control system allows the cleaning mechanism to be lowered down to the rim of a reaction cup to inject water into the reaction cup through an injection device of the cleaning mechanism, thereby completing the water injection step. Then, the control system allows the cleaning mechanism to be lowered down to the bottom of the reaction cup, activates the waste pump and opens the waste valve such that water in the reaction cup is pumped out into the effluent container through the waste pipeline, thereby completing the water discharge step. The cleaning of the waste pump and valve can be done by repeating the above steps one or more times.

In the present embodiment, the biochemical analyzer has two reagent adding mechanisms and one sample adding mechanism. However, biochemical analyzers having a single or more than two reagent adding mechanisms and two or more sample adding mechanisms are also applicable. Furthermore, the components of the biochemical analyzer and the relative relationship of the components are not limited to the above.

The automatic cleaning of such fluid components as the waste pump and waste valve is achieved by providing the biochemical analyzer with a cleaning mode. The cleaning may be performed by conducting the water injection step and the water discharge step each once in a cycle, and repeating the cycles, or by periodic water injection but continuous water discharging, or any other sequence capable of cleaning the fluid components automatically by means of water injection and water discharge. Additionally, the automatic cleaning may be performed by means of water injection and discharge via only one reaction cup or via a plurality of reaction cups through coordination of the relevant mechanisms, reaction disc, sample disc and reagent disc.

A method of cleaning fluid components of a biochemical analyzer, the biochemical analyzer having a reagent adding mechanism, a sample adding mechanism, at least one reaction cup, a cleaning mechanism and a waste pipeline connected to the cleaning mechanism, a waste pump being arranged on the waste pipeline, each of the reagent adding mechanism, the sample adding mechanism, the cleaning mechanism and the waste pump being connected to a control system, wherein the control system has a cleaning mode comprising: a) a water injection step in which the control system allows at least one of the reagent adding mechanism, the sample adding mechanism and the cleaning mechanism to inject water into the reaction cup; and b) a water discharge step in which the control system allows the reaction cup, the cleaning mechanism and the waste pipeline to be in fluid communication, and activates the waste pump to discharge water from the reaction cup through the cleaning mechanism and the waste pipeline. By adding an additional cleaning mode, this cleaning method does not require the existing working sequence of sample adding, reagent adding, stiffing, cleaning and effluent discharging of the biochemical analyzer to be changed. The cleaning of the fluid components such as the water pump and the waste valves in the waste pipeline may be accomplished automatically without manual intervention by performing said water injection and water discharge one or more times. This eliminates the need to disassemble the precise fluid components for maintenance, thereby saving maintenance time and reducing maintenance cost, ensuring the reliability of fluid components, and avoiding biological contamination. The biochemical analyzer may be a fully-automatic biochemical analyzer or a semi-automatic biochemical analyzer, preferably a fully-automatic biochemical analyzer. The water used for cleaning is preferably deionized water.

In accordance with the method of cleaning fluid components of the biochemical analyzer, in step a), the control system allows the cleaning mechanism to inject water into the reaction cup; in step b), the control system allows the reaction cup, the cleaning mechanism and the waste pipeline to be in fluid communication by lowering the cleaning mechanism into the reaction cup. Specifically, in step a), the cleaning mechanism is lowered to the rim of the reaction cup to discharge water into the reaction cup under the control of the control system; in step b), the control system allows the reaction cup, the cleaning mechanism and the waste pipeline to be in fluid communication by lowering the cleaning mechanism to the bottom of the reaction cup.

Alternatively, in step a), the control system allows the reagent adding mechanism or sample adding mechanism to inject water into the reaction cup; in step b), the control system allows the reaction cup, the cleaning mechanism and the waste pipeline to be in fluid communication by lowering the cleaning mechanism into the reaction cup. Specifically, in step a), the cleaning mechanism is held above the reaction cup, while the reagent adding mechanism or sample adding mechanism injecting water into the reaction cup; in step b), the control system allows the reaction cup, the cleaning mechanism and the waste pipeline to be in fluid communication by lowering the cleaning mechanism to the bottom of the reaction cup. The step a) and step b) are repeated at least twice.

The waste pipeline is provided with at least one waste valve connected to the control system for connecting/disconnecting the waste pipeline. In both step a) and step b), the water employed is deionized water.

A better cleaning effect may be achieved by repeating the above cleaning steps, thereby more effectively avoiding the effect of the complex elements on the fluid components such as waste pump and waste valve, etc.

Under the effect of water flushing, the deposition of elements such as fat and protein onto the pump and valve can be avoided. The problem of detergent crystallization is also avoided as the detergent on the pump and valve is dissolved by the water and discharged out of the biochemical analyzer. By flushing the membranes of the pump and valve with water, corrosion of the membranes by organic substances is also avoided.

While the present invention has been described in detail with reference to preferred embodiments, the present invention should not be construed as being limited to the preferred embodiments. Persons skilled in the art understand that various changes and substitutions may be made without departing from the spirit and scope of the present invention.

The invention claimed is:

1. A method for cleaning fluid components of a biochemical analyzer, comprising:
adding sample, adding reagent, and cleaning reaction cups, further comprising a cleaning mode after the reaction cups are cleaned, the cleaning mode comprising:
injecting water, cleaning fluid, or cleaning solution into a reaction cup of the biochemical analyzer without disassembly of the biochemical analyzer, one or more of a cleaning mechanism, a reagent adding mechanism, and a sample adding mechanism are used to inject the water, cleaning fluid, or cleaning solution into the reaction cup;
discharging the water, cleaning fluid, or cleaning solution from the reaction cup using a waste pump, wherein the reaction cup, a cleaning mechanism, and a waste pipeline are in fluid communication with each other by actuating at least a part of the cleaning mechanism into the reaction cup; and
repeating the act of injecting and the act of discharging a plurality of iterations.

2. The method according to claim 1, wherein the cleaning mechanism is actuated to the reaction cup to inject the water, cleaning fluid, or cleaning solution into the reaction cup under control of a control system, and the control system allows the reaction cup, the cleaning mechanism, and the waste pipeline to communicate with each other by actuating at least the part of the cleaning mechanism to a bottom portion of the reaction cup.

3. The method according to claim 1, wherein a reagent adding mechanism or a sample adding mechanism is used to inject water, cleaning fluid, or cleaning solution into the reaction cup, further comprising actuating the cleaning mechanism to a position above the reaction cup for the reagent adding mechanism or the sample adding mechanism to inject the water, cleaning fluid, or cleaning solution into the reaction cup.

4. The method according to claim 1, wherein the waste pipeline is used to discharge the water, cleaning fluid, or cleaning solution, and the waste pipeline is provided with at least one waste valve for connecting or disconnecting the waste pipeline.

5. The method according to claim 1, wherein the water, cleaning fluid, or cleaning solution comprises deionized water.

* * * * *